United States Patent [19]

Iwashita

[11] Patent Number: 4,624,133
[45] Date of Patent: Nov. 25, 1986

[54] APPARATUS FOR DETERMINING THE CONCENTRATION OF OIL IN ANOTHER LIQUID

[75] Inventor: Yoshiaki Iwashita, Kyoto, Japan

[73] Assignee: Horiba, Ltd., Kyoto, Japan

[21] Appl. No.: 726,379

[22] Filed: Apr. 23, 1985

[30] Foreign Application Priority Data

Apr. 24, 1984 [JP] Japan .................. 59-82313

[51] Int. Cl.$^4$ .......................................... G01N 33/18
[52] U.S. Cl. .................. 73/61.1 R; 250/301
[58] Field of Search ............ 73/61.1 R; 250/301, 250/343

[56] References Cited

U.S. PATENT DOCUMENTS

| | | | |
|---|---|---|---|
| 3,627,419 | 12/1971 | Thevenier | 73/61.1 R X |
| 3,924,449 | 12/1975 | Moreau et al. | 73/61.1 R |
| 4,103,162 | 7/1978 | Iwamoto et al. | 250/343 |
| 4,164,653 | 8/1979 | Matumoto et al. | 250/301 |
| 4,207,450 | 6/1980 | Mittleman | 250/301 X |

FOREIGN PATENT DOCUMENTS 111412 7/1982 Japan .................. 250/343

Primary Examiner—Stewart J. Levy
Assistant Examiner—Joseph W. Roskos
Attorney, Agent, or Firm—Wenderoth, Lind & Ponack

[57] ABSTRACT

An apparatus for determining the concentration of oil in another liquid has an oil extracting apparatus for mixing a sample of oil containing liquid and an oil-extracting solvent, a source of solvent, a solvent pump having the intake side connected to the source of solvent and the discharge side connected to the oil extracting apparatus for pumping oil extracting solvent from the source of solvent along a solvent flow path into the oil extracting apparatus, a water pump for pumping a liquid containing oil therein into the oil extracting apparatus, a separator for receiving the mixture of oil, water and solvent from the oil extracting apparatus and separating the oil-containing solvent therefrom, and an analyzer for analyzing the oil-containing solvent for oil content. A solvent supply pipe is connected between the solvent flow path and the intake side of the water pump means and includes a control therein for limiting the amount of solvent flowing therethrough to an amount less than supplied from the solvent pump to the oil extracting apparatus.

5 Claims, 3 Drawing Figures

APPARATUS FOR DETERMINING THE CONCENTRATION OF OIL IN ANOTHER LIQUID

BACKGROUND OF THE INVENTION

1. Field of the Invention

The present invention relates to an apparatus for determining the concentration of oil in another liquid, which apparatus is especially useful for measuring the concentration of oil contained in industrial waste water anc river water.

2. Description of the Prior Art

An apparatus for determining the concentration of oil contained in various kinds of water is known from U.S. Pat. No. 4,103,162. It comprises an extraction apparatus for introducing into an extractor a sample of an oil-containing water and an amount of an oil-extracting solvent by means of a pump. The separator separates the liquid mixture in said extractor into said solvent and the sample water, and an analyzer is used for analyzing the separated solvent containing oil therein to determine the concentration of oil.

Such an apparatus for determining the concentration has disadvantages which have a bad influence upon the measurement. For example, oils and oily suspensions, such as plankton, contained in the sample of water to be measured adhere to portions of the pump for introducing the sample of water into the extraction apparatus which portions are contacted by the liquids. In the case of a diaphragm pump, these portions are the diaphragm, check valve and the like where the flowing speed is suddenly changed. This has an influence upon the stability of the pump during discharge, and accumulations sometimes come off and produce noises.

SUMMARY OF THE INVENTION

The present invention has as its purpose the prevention of the adherence of foreign bodies to the portions of the pump contacted by the liquids. This is accomplished by a simple improvement in the apparatus for determining the concentration of oil, the improvement being a pipe for adding a part of said oil-extracting solvent which is to be introduced into said extraction apparatus, said pipe being connected with the upper part of the pump for pumping the sample water into said extraction apparatus.

By this means, the pump for introducing a sample of water into the extractor can be stably operated for a long time and highly reliable measurement values can be obtained. This is believed to be because the portions of the pump which are contacted by the liquids are rinsed with the oil-extracting solvent as a part of said oil-extracting solvent passes through said pump together with said sample water, whereby the adherence of oils and the like to said portions contacted by liquids as well as the growth of accumulations on said portions can be effectively prevented. Thus a part of said oil-extracting solvent, which is basically used for determining the concentration of oil, is also effectively used as a means for preventing build-ups in the pump.

BRIEF DESCRIPTION OF THE DRAWINGS

The drawings illustrate the preferred embodiments of the present invention, in which.

DESCRIPTION OF THE PREFERRED EMBODIMENTS

Figure 1:
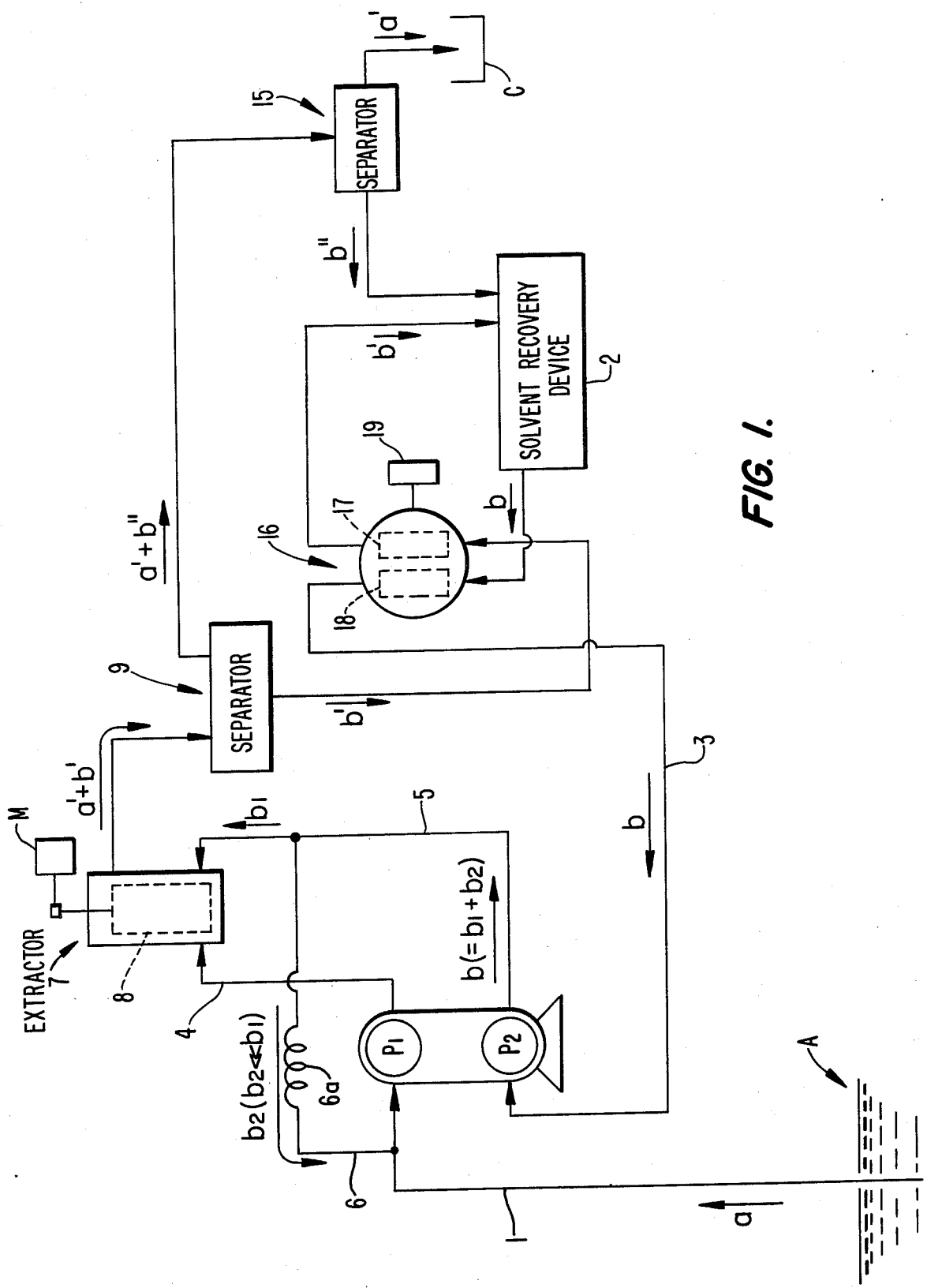
FIG. 1 is a general block diagram showing an apparatus for determining the concentration of oil in another liquid.

The preferred embodiments of the present invention will be described with reference to the drawings. Referring now to FIG. 1, which is a general block diagram showing an apparatus for continuously determining the concentration of oil in another liquid, one pump $P_1$ of a pair of diaphragm type quantitative pumps $P_1$ and $P_2$ has a suction pipe 1 with the end extending into a stream A of water such as industrial waste waters containing oils therein for sucking the sample water a containing oil from said stream A into the inlet side of pump $P_1$, and the other pump $P_2$ is provided with a solvent-suction pipe 3 for sucking of oil-extracting solvents b, (for example, $CCl_4$ or $Cl(CF_2-CFCl)_2Cl$, as disclosed in U.S. Pat. No. 4,164,653) from a solvent-regenerator 2 which will be described later, connected with the inlet side of pump $P_2$. Pump $P_1$ is provided with a discharge pipe 4 from the outlet side thereof, and pump $P_2$ is provided with a discharge pipe 5 from the outlet side thereof. A solvent adding pipe 6 having a flow control means 6a, such as a smaller diameter than pipe 5 is connected between said pipe 5 and said sample water-suction pipe 1 for adding a small amount of oil-extracting solvent $b_2$ to the sample of water a, the amount being less than $b_1$.

An oil extracting apparatus 7 has said discharge pipes 4 and 5 connected thereto, and is provided with stirring blades 8 driven by a motor M for mixing said water sample a, which is supplied by said pump $P_1$, with said oil-extracting solvent which is supplied by means of said pump $P_2$, to extract oils contained in said sample of water a by means of said solvent b. The desired total amount of solvent b supplied through said pump $P_2$ is supplied to said oil extracting apparatus, the portion $b_1$ being directly introduced and the portion $b_2$ being delivered into the sample liquid a through pipe 6 and introduced with the sample liquid a.

A first separator 9 is connected to said extracting apparatus 7 for receiving the liquid mixture $a'+b'$ and carries out the primary separation of said liquid mixture into a solvent $b'$, which contains extracted oil, and sample water $a'$ from which oil has been removed and a small amount of solvent $b''$.

Figure 2:
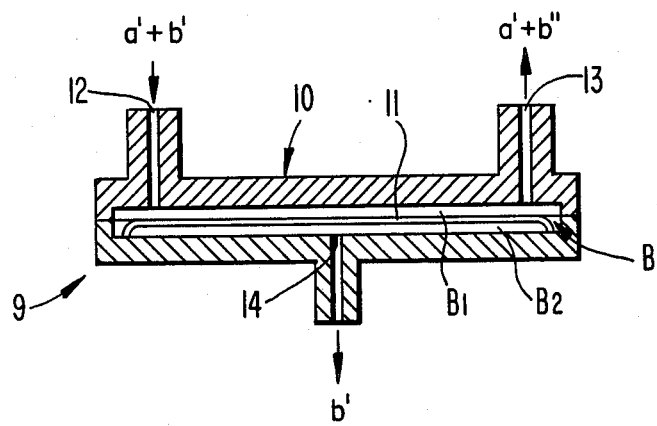
FIG. 2 is a schematic sectional view of the first separator.

One example of the structure of said first separator 9 is shown in FIG. 2. A space B is provided within a body 10 of said first separator 9, said space B being divided into upper and lower parts $B_1$ and $B_2$ by a hydrophobic filter 11. The upper part $B_1$ is provided with an inlet 12 for said liquid mixture at one end thereof and an outlet 13 for the sample water $a'$ containing a small amount of solvent $b''$ at other end thereof. The lower space $B_2$ is provided with an outlet 14 for the solvent $b'$ at the central portion thereof.

A second separator 15 is provided and is connected to said outlet 13 to receive the sample water $a'$ and the small amount of solvent $b'$, and separates the sample water $a'$ and discharges it, for example into a drain tank c.

The solvent $b'$ is introduced into a regenerator 2 from the separator 9 through an analyzer 16, and solvent $b''$ is supplied from said separator 15, and the solvent b is supplied through the analyzer 16 to the pump $P_2$.

The regenerator 2 comprises a body filled with activated carbon in which the solvent is regenerated by removing oils from said solvent by the adsorption method.

The analyzer 16 is for determining the concentration of oil, and is provided with a measuring cell 17 through which said solvent b′ from said first separator 9 is passed and a reference cell 18 through which regenerated solvent b is passed. The concentration of oil extracted by the solvent b′ is recorded by a recorder 19. By passing the regenerated solvent b through said reference cell 18, an error of measurement due to a deterioration of the performance of said regenerator 2 is prevented from occurring.

By an apparatus of the above-described construction, the concentration of oils contained in said sample water a can be continuously determined, and the oil-extracting solvent b is regenerated and used repeatedly. The portions of said sample water-introducing pump $P_1$ contacted by liquids are continuously rinsed with said solvent b by the part thereof passed back through pipe 6 to the intake of pump $P_1$ while the sample is taken into said sample-water introducing pump $P_1$. That is to say, the concentration of oils is being determined, while oils and oily suspensions such as plankton, are effectively prevented from adhering to the portions of the pump $P_1$ contacted by the sample liquids, whereby the pump $P_1$ can be caused to operate stably and at the same time the measurement accuracy can be improved.

In addition, only a part of said solvent b′ from said first separator 9 is introduced into the analyzer 16, while the rest joined with the portion b″ in said regenerator 2. Alternatively, all of said solvent b′+b″ may be into said regenerator 2 at one time by joining said solvent b′ from said first separator 9 and that from said second separator 15 or providing only one separator.

Further, although flow type separators are used as separators 9 and 15 in the above-described preferred embodiment, separators of the stand still-separation type may be used, and the construction can be such as to take a part of said separated solvent out of the system and replace a corresponding amount of said solvent b in said solvent-suction pipe 3.

Furthermore, although the solvent-adding pipe 6 having a smaller diameter is shown as being connected with the upper reaches of said sample water-introducing pump $P_1$ in the above-described preferred embodiment, the flow control means can be a choke orifice.

Figure 3:
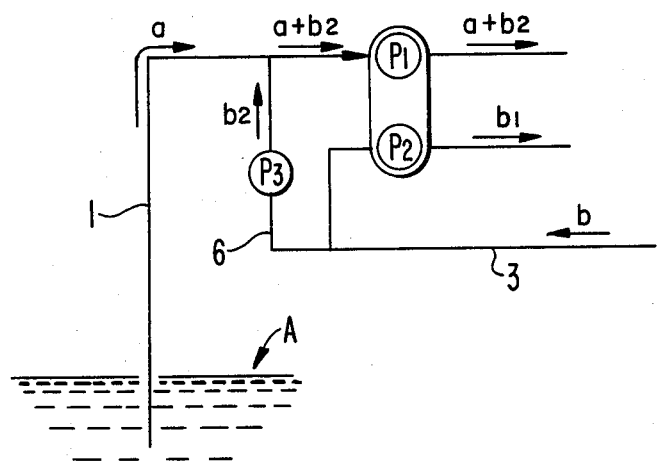
FIG. 3 is a block diagram showing another preferred embodiment wherein solvents are added in another manner.

Alternatively, as shown in FIG. 3, the solvent-adding pipe 6 can be connected on the intake side of pump $P_2$ and suction pipe 1 for pump $P_1$, and a flow control means in the form of a third pump $P_3$ having a small capacity and which is a quantitative type can be provided in pipe 6, and the other end can be connected to the suction pipe 1 of said pump $P_1$.

What is claimed is:

1. An apparatus for determining the concentration of oil in another liquid, comprising:
   an oil extracting apparatus for mixing a sample of oil containing liquid and an oil-extracting solvent;
   a source of solvent;
   solvent pump means having the intake side connected to said source of solvent and the discharge side connected to said oil extracting apparatus for pumping oil extracting solvent from said source of solvent along a solvent flow path into said oil extracting apparatus;
   water pump means having the discharge side connected to said oil extracting apparatus for pumping a liquid containing oil therein into said oil extracting apparatus;
   a separator means connected to said oil extracting apparatus for receiving the mixture of oil, water and solvent from said oil extracting apparatus and separating the oil-containing solvent therefrom;
   an analyzer means connected to said separator means for receiving the oil-containing solvent and analyzing it for oil content; and
   solvent supply pipe means connected between said solvent flow path and the intake side of said water pump means and including a control means therein for limiting the amount of solvent flowing therethrough to an amount less than supplied from said solvent pump means to said oil extracting apparatus.

2. An apparatus as claimed in claim 1 in which said solvent supply pipe means is connected between the discharge side of said solvent pump means and the intake side of said water pump means.

3. An apparatus as claimed in claim 2 in which said solvent supply pipe means has a smaller diameter than the flow path from said solvent pump means to said oil extracting apparatus.

4. An apparatus as claimed in claim 2 in which said solvent supply pipe means has a choke orifice therein.

5. An apparatus as claimed in claim 1 in which said solvent supply pipe means is connected between the intake side of said solvent pump means and the intake side of said water pump means, and said control means is a further solvent pump means.

* * * * *